United States Patent [19]

Pioch

[11] 4,264,521

[45] Apr. 28, 1981

[54] 5-HALO-4-OXO-2-PHENYLPENTANENI-TRILES

[75] Inventor: Richard P. Pioch, Indianapolis, Ind.

[73] Assignee: Eli Lilly and Company, Indianapolis, Ind.

[21] Appl. No.: 154,654

[22] Filed: May 30, 1980

[51] Int. Cl.³ .................. C07C 121/76; C07D 233/64
[52] U.S. Cl. ........................ 260/465 G; 424/273 R; 548/342
[58] Field of Search .................. 260/465 G; 548/342; 424/273 R

[56] References Cited

U.S. PATENT DOCUMENTS

| 4,009,021 | 2/1977 | Yih et al. ..................... 548/342 X |
| 4,073,921 | 2/1978 | Miller et al. .................. 424/273 R |
| 4,115,578 | 9/1978 | Miller et al. .................. 424/273 R |

OTHER PUBLICATIONS

McDonald et al., *J. Org. Chem.*, vol. 35, pp. 1250–1254 (1970).

*Primary Examiner*—Dolph H. Torrence
*Attorney, Agent, or Firm*—Joseph A. Jones; Arthur R. Whale

[57] ABSTRACT

A series of 5-halo-4-oxo-2-phenylpentanenitriles are useful as intermediates for preparing 3-(imidazol-4-yl)-2-phenylpropanenitriles, which are useful as fungicides.

11 Claims, No Drawings

5-HALO-4-OXO-2-PHENYLPENTANENITRILES

BACKGROUND OF THE INVENTION

1. Field of the Invention

This invention pertains to organic chemistry, and especially to agricultural chemistry. It provides novel intermediates used for preparing antimicrobial 3-(imidazol-4-yl)-2-phenylpropanenitriles, used for control of powdery mildew of plants.

SUMMARY OF THE INVENTION

This invention provides a series of compounds of the formula

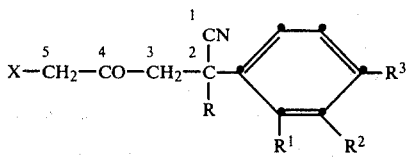

wherein X is chloro or bromo;
R is $C_1$–$C_4$ alkyl, phenyl or phenyl mono(3- or 4-)-substituted with methyl, bromo, chloro, fluoro or trifluoromethyl;
$R^1$ is hydrogen, chloro, bromo or fluoro;
$R^2$ is hydrogen, methyl, bromo, chloro, fluoro or trifluoromethyl;
$R^3$ is hydrogen, methyl, bromo, chloro, fluoro or trifluoromethyl;
provided that one or both of $R^2$ and $R^3$ is hydrogen; and that $R^1$ is an atom other than hydrogen only when $R^3$ is chloro, bromo or fluoro.

The compounds are intermediates used in chemical synthesis, as will be explained below.

DESCRIPTION OF THE PREFERRED EMBODIMENTS

In the above general formula, the term "$C_1$–$C_4$ alkyl" includes the groups methyl, ethyl, propyl, isopropyl, butyl, s-butyl, i-butyl, and t-butyl.

Certain classes of the compounds of this invention constitute preferred embodiments of the invention. For example, the following groups of compounds include such preferred embodiments. It will be understood that the various classes below may be combined to define further preferred groups of compounds.

(1) R is phenyl;
(2) $R^1$ is hydrogen;
(3) either $R^2$ or $R^3$ is bromo, chloro, methyl or trifluoromethyl;
(4) $R^2$ is hydrogen;
(5) $R^2$ or $R^3$ is methyl;
(6) R is phenyl or substituted phenyl.

The preferred compounds of this invention are 2-butyl-5-chloro-4-oxo-2-phenylpentanenitrile, 5-chloro-4-oxo-2,2-diphenylpentanenitrile, 5-chloro-2-(4-methylphenyl)-4-oxo-2-phenylpentanenitrile, 5-chloro-2-(4-chlorophenyl)-4-oxo-2-phenylpentanenitrile, 5-chloro-2,2-bis(4-chlorophenyl)-4-oxopentanenitrile, 5-chloro-4-oxo-2-phenyl-2-(4-trifluoromethylphenyl)-pentanenitrile, and 2-(4-bromophenyl)-5-chloro-4-oxo-2-phenylpentanenitrile.

It is believed that the above general formula clearly explains the compounds of this invention, but a group of representative compounds will be mentioned to assure the reader's understanding.

5-chloro-2-(2-chloro-4-methylphenyl)-2-methyl-4-oxopentanenitrile
5-bromo-2-(2,4-dibromophenyl)-2-(i-butyl)-4-oxopentanenitrile
5-bromo-2-(2-fluoro-4-bromophenyl)-4-oxo-2-propylpentanenitrile
2-(s-butyl)-5-chloro-2-(3-methylphenyl)-4-oxopentanenitrile
5-bromo-2-(2,4-difluorophenyl)-4-oxo-2-phenylpentanenitrile
5-bromo-2-(4-bromophenyl)-2-(3-methylphenyl)-4-oxopentanenitrile
2-(4-bromophenyl)-5-chloro-2-(3-chlorophenyl)-4-oxopentanenitrile
5-chloro-2-(3-chlorophenyl)-2-(4-fluorophenyl)-4-oxopentanenitrile
5-chloro-2-(3-fluorophenyl)-2-(3-trifluoromethylphenyl)-4-oxopentanenitrile
5-bromo-4-oxo-2-(3-trifluoromethylphenyl)-2-(4-trifluoromethylphenyl)pentanenitrile The pentanenitriles of this invention are prepared by reacting a pentenenitrile of the formula

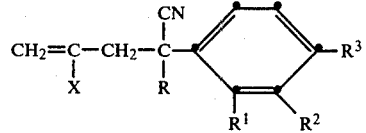

with an oxidizing agent at elevated temperature in the presence of a free radical inhibitor, and the pentenenitriles are prepared by reacting a phenylacetonitrile having the R through $R^3$ substituents of the pentanenitrile with a 2,3-dihalopropene.

In the first step, a 2,3-dihalopropene of the formula

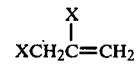

is reacted with a phenylacetonitrile of the formula

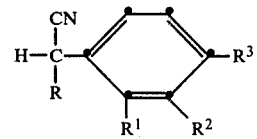

wherein the substituents are as defined above in the definition of the pentanenitriles. The reaction is carried out in the presence of a strong base in an inert organic solvent, such as an ether, including diethyl ether and tetrahydrofuran, an amide such as dimethylformamide, dimethylacetamide or N-methyl-2-pyrrolidone, or an aromatic, such as benzene, toluene, the xylenes, and the like.

The strong bases used in the process are chosen from the commonly used reagents such as the alkali metal hydrides, the alkyllithiums, especially butyllithium, the alkali metal alkoxides, and the alkali metal amides. The term "alkali metal" is used here to refer to sodium, potassium and lithium, and the alkoxy groups referred to are those containing from 1 to 4 carbon atoms in each case.

The preferred strong base is sodium hydride, and the preferred solvent is dimethylformamide. The base is first reacted with the phenylacetonitrile, and the dihalopropene is then reacted with the resulting carbanion. The reaction temperature is from about 0° C. to about 100° C., preferably from about the ambient temperature to about 75° C. The reaction is complete in from about 15 minutes to about 24 hours, preferably from about 1 to about 4 hours. Equimolar amounts of the reactants and the base are used, and no excess reactant is necessary, but excess reactants may be used where it is convenient to assure that one of the reactants, usually the more expensive one, is fully utilized.

The pentenenitrile so produced is isolated readily by filtering insoluble inorganics from the reaction mixture and evaporating down to remove the solvent. The intermediate product is used without purification, other than simple water-washing to remove any residue of the base or hydrohalide.

The pentenenitriles are oxidized with an oxidizing agent to form the pentanenitriles. The preferred oxidizing agent is 3-chloroperbenzoic acid; the best oxidizing agents, in general, are organic "per" acids, such as peracetic acid and perbenzoic acid.

It is necessary to use a radical inhibitor in the reaction mixture. A preferred inhibitor is bis(3-t-butyl-4-hydroxy-5-methylphenyl) sulfide. Other radical inhibitors are also used including such known compounds as 2,6-bis(t-butyl)-4-methylphenol, 4,4'-butylidenebis(6-t-butyl-3-methylphenol), and dilauryl 3,3-thiodipropionate.

Only a catalytic amount of the radical inhibitor is needed in the reaction mixture. An excess amount of the oxidizing agent is preferably used in the reaction, such as about 20-50% excess or even a very large excess, such as 10X. The excess amount which should be used, of course, depends on the relative economics of the oxidizing agent and the pentenenitrile.

The oxidation is preferably carried out in a halogenated hydrocarbon, such as chloroform, dichloroethane and the like, at temperatures in the range from about 50° C. to about 100° C.

While the present invention does not depend on the reaction mechanism, it is believed that the pentanenitriles are formed in two steps. The pentenenitrile is first converted to a 4,5-epoxy-4-halopentanenitrile, which then rearranges to form the desired product. See McDonald and Steppel, J. Org. Chem. 35, 1250–54 (1970).

The pentanenitrile is isolated by reducing the remaining oxidizing agent left at the end of the process, and then washing the reaction mixture with a mild base such as dilute aqueous sodium bicarbonate solution. The washed organic layer is then evaporated to dryness and the residue, containing the intermediate product, is dissolved in fresh solvent and filtered to obtain a solution of the intermediate pentanenitrile.

The following preparative examples are provided to assure that the method of obtaining the compounds of this invention is understood, and that the reader can obtain any desired compound.

PREPARATION 1

2-butyl-4-chloro-2-phenyl-4-pentenenitrile

A 7.62 g. portion of 2-phenylhexanenitrile and 2.11 g. of 50% sodium hydride were combined in 30 ml. of dry dimethylformamide, and the mixture was stirred for 1.5 hours at 50°-55° C. The mixture was then cooled to 20° C. and 4.88 g. of 2,3-dichloro-1-propene was added dropwise, followed by an additional 10 ml. of dry dimethylformamide. The reaction mixture warmed spontaneously to about 35° C., and it was warmed to 55° C. after the addition and was stirred at that temperature for 1.5 hours. The mixture was then allowed to cool to ambient temperature and was stirred for 64 hours. It was then filtered to remove insoluble inorganics, and the solids were washed with ethyl acetate. The filtrate was evaporated under vacuum to an oil, which was dissolved in diethyl ether and was washed with water. The residue was taken up in ethanol and evaporated to dryness under vacuum to obtain 10.85 g. of the crude product named in the heading above. The product was identified by 60 mHz nuclear magnetic resonance analysis in $CDCl_3$: $\delta$7.37 (m, 5H); 5.25 (d, 1H, J=2 Hz); 5.08 (d, 1H, J=2 Hz); 2.93 (s, 2H); 1.97 (dt, 2H); 1.25 (m, 4H); 0.83 (t, 3H).

PREPARATION 2

4-chloro-2,2-diphenyl-4-pentenenitrile

A 40.3 g. portion of sodium amide was suspended in 400 ml. of dry toluene at 70° C. and 199.6 g. of diphenylacetonitrile, dissolved in 600 ml. of hot dry toluene, was added dropwise. The mixture was stirred at 70°–100° C. for 4 hours, and an additional 500 ml. of dry toluene and 100 ml. of dimethylformamide were added. The mixture was stirred for 27 hours more. The slurry was cooled to 10° C., and 114.6 g. of 2,3-dichloropropene was added. The mixture was warmed to ambient temperature and stirred for 40 hours, and was then stirred at 90°100° C. for one hour. The mixture was then cooled to ambient temperature, diluted with a large amount of diethyl ether, washed with water and dried over magnesium sulfate. The solution was evaporated to give 265 g. of crude liquid product.

EXAMPLE 1

2-butyl-5-chloro-2-phenyl-4-oxopentanenitrile

The intermediate product made in Preparation 1 was combined with 0.17 g. of bis(3-t-butyl-4-hydroxy-5-methylphenyl) sulfide in 100 ml. of 1,2-dichloroethane, and the mixture was heated to the reflux temperature. To it was added 12.31 g. of 3-chloroperbenzoic acid in 110 ml. of warm 1,2-dichloroethane, dropwise. The mixture was stirred at the reflux temperature for 40 hours. An additional 6.16 g. of 3-chloroperbenzoic acid and 0.20 g. of the sulfide dissolved in 50 ml. of 1,2-dichloroethane were added, and the reflux was continued for a total of 69 hours. The reaction mixture was then cooled, and to it was added, dropwise, 250 ml. of 10% sodium sulfite solution, followed by 9 g. of sodium bicarbonate dissolved in 100 ml. of water. The organic layer was separated and washed with water, and was then evaporated to dryness under vacuum. The residue was taken up in ethanol and evaporated to dryness under vacuum, and that step was repeated twice more. The residue was then taken up in 1,2-dichloroethane and filtered, and the filtrate was evaporated to dryness to obtain 12.35 g. of crude product, which was identified by 60 mHz nuclear magnetic resonance analysis in $CDCl_3$, showing the following characteristic peaks: $\delta$7.38 (m, 5H); 3.88 (s, 2H); 3.32 (s, 2H); 1.97 (dt, 2H); 1.25 (m, 4H); 0.85 (t, 3H).

EXAMPLE 2

5-chloro-4-oxo-2,2-diphenylpentanenitrile

A 265 g. portion of 4-chloro-2,2-diphenyl-4-pentenenitrile and 3.84 g. of bis(3-t-butyl-4-hydroxy-5-methylphenyl) sulfide were dissolved in 1 liter of 1,2-dichloroethane and heated to the reflux temperature, about 75°-80° C. To the mixture was added dropwise a solution of 276.9 g. of 3-chloroperbenzoic acid dissolved in 2.5 liters of 1,2-dichloroethane. The resulting solution was heated for 24 hours, and was then cooled to ambient temperature. Sodium sulfite solution was added until starch-iodide paper showed a negative test for peracid. The reaction mixture was then made basic by the addition of 135 g. of sodium bicarbonate in saturated aqueous solution, and the organic layer was then separated, washed with water and dried over sodium sulfate. The solvent was then evaporated away under vacuum to obtain 294.5 g. of crude product, which was crystallized from ethanol to obtain 194.3 g. of the product named in the heading, m.p. 102°-104° C.

The compounds of this invention are used as intermediates in the preparation of a series of 3-(imidazol-4-yl)-2-phenylpropanenitriles of the formula

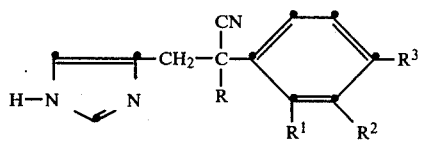

and the non-phytotoxic acid addition salts thereof, which compounds are further discussed in the U.S. patent application Ser. No. 154,653 of Richard Pioch and Leander Merritt, which application was filed on the same day as the present application. The above compounds are used for the control of powdery mildew of plants.

The fungicidal compounds described above are prepared from the pentanenitriles of this invention by reacting a pentanenitrile with formamide, either neat or in an inert organic solvent. It is preferred not to use a solvent other than the formamide itself. At least 2 moles of formamide are needed per mole of pentanenitrile. Excess amounts of formamide may be used as desired, and it is preferred to use a sufficient amount of formamide to make a stirrable reaction mixture. For example, from about 5 to about 25 moles of formamide are preferred. The preferred reaction temperature is the reflux temperature of the reaction mixture in neat formamide, most preferably about 200° C. A temperature range from about 150° C. to about 200° C. is effective, however.

Reaction times in the range of a few hours are preferred, preferably from about ½ hour to about 6 hours; reaction times from about 15 minutes to about 24 hours are used in various instances, as may be convenient.

The fungicidal product is isolated from the reaction mixture by evaporating the solvent, if any, and any excess formamide which may remain, under vacuum, and partitioning the residue between water and an organic solvent such as diethyl ether. The organic layer is then washed with additional portions of water, and the organic layer, containing the product in the free base form, is evaporated to dryness, or the product is converted to the desired salt, depending on the form in which the product is desired.

The following preparations are provided to assure that the reader can obtain the fungicides from the compounds of this invention.

PREPARATION 3

3-(imidazol-4-yl)-2,2-diphenylpropanenitrile

A 5.68 g. portion of the product of Example 2 above was dissolved in 20 ml. of formamide, and was stirred at the reflux temperature for 2 hours. The mixture was evaporated to a gum under vacuum, and the gum was shaken with a mixture of diethyl ether and sodium hydroxide solution. The organic layer was extracted with dilute hydrochloric acid, and the acid layer was extracted with diethyl ether, and made basic with dilute sodium hydroxide solution. The basic solution was extracted with diethyl ether and evaporated under vacuum to obtain 3.2 g. of the free base named above, in crude form. The free base was reacted with 1.43 g. of maleic acid to obtain 2.58 g. of the maleate salt of the product named above, m.p. 156.5°-158.5° C., after it had been crystallized twice from acetone.

PREPARATION 4

3-(imidazol-4-yl)-2-butyl-2-phenylpropanenitrile

The product of Example 1 above was added to 50 ml. of formamide and the mixture was stirred at the reflux temperature for 3.75 hours. The excess formamide was then removed under vacuum, and the residue was partitioned in a diethyl ether/water mixture. The organic layer was separated and washed with water until the wash liquid was clear. The ether solution was then extracted with 100 ml. of 1 N hydrochloric acid, and was washed with water. The two aqueous extracts were combined, and were extracted with diethyl ether until the extract was clear. The aqueous layer was then made basic with 5 N sodium hydroxide solution, and was extracted again with diethyl ether. The ether extract was dried over sodium sulfate, filtered, and evaporated to dryness to give 3.7 g. of crude product. Mass spectroscopic analysis showed a molecular ion of weight 253. The material was converted to the oxalate salt by dissolving it in a large volume of diethyl ether with oxalic acid. The crude product amounted to 4.4 g. of insoluble solid, which was recrystallized from acetone/ethyl acetate to obtain 3.8 g. of the oxalate salt of the product named above, m.p. 143°-150° C. The salt was dissolved in methanol, decolorized with activated charcoal and recrystallized from isopropanol/ethyl acetate to obtain 2.44 g. of purified oxalate salt, m.p. 150°-153° C. dec.

I claim:
1. A compound of the formula

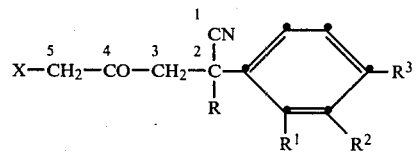

wherein X is chloro or bromo;
R is $C_1$-$C_4$ alkyl, phenyl or phenyl mono(3- or 4)-substituted with methyl, bromo, chloro, fluoro or trifluoromethyl;
$R^1$ is hydrogen, chloro, bromo or fluoro;

$R^2$ is hydrogen, methyl, bromo, chloro, fluoro or trifluoromethyl;

$R^3$ is hydrogen, methyl, bromo, chloro, fluoro or trifluoromethyl; provided that one or both of $R^2$ and $R^3$ is hydrogen; and that $R^1$ is an atom other than hydrogen only when $R^3$ is chloro, bromo or fluoro.

2. A compound of claim 1 wherein $R^1$ is hydrogen.

3. A compound of claim 1 or claim 2 wherein R is phenyl or substituted phenyl.

4. A compound of claim 3 wherein either $R^2$ or $R^3$ is bromo, chloro, methyl or trifluoromethyl.

5. The compound of claim 1 which is 2-butyl-5-chloro-4-oxo-2-phenylpentanenitrile.

6. The compound of claim 1 which is 5-chloro-4-oxo-2,2-diphenylpentanenitrile.

7. The compound of claim 1 which is 5-chloro-2-(4-methylphenyl)-4-oxo-2-phenylpentanenitrile.

8. The compound of claim 1 which is 5-chloro-2-(4-chlorophenyl)-4-oxo-2-phenylpentanenitrile.

9. The compound of claim 1 which is 5-chloro-2,2-bis(4-chlorophenyl)-4-oxopentanenitrile.

10. The compound of claim 1 which is 5-chloro-4-oxo-2-phenyl-2-(4-trifluoromethylphenyl)-pentanenitrile.

11. The compound of claim 1 which is 2-(4-bromophenyl)-5-chloro-4-oxo-2-phenylpentanenitrile.

* * * * *